US010739217B2

(12) United States Patent
Hardy et al.

(10) Patent No.: US 10,739,217 B2
(45) Date of Patent: Aug. 11, 2020

(54) METHOD AND APPARATUS FOR EMERGENCY BRAKING PERFORMANCE TESTING, EVALUATION AND/OR DRIVER TRAINING

(71) Applicant: CW & SR INVESTMENTS PTY LTD, Coleambally (AU)

(72) Inventors: Christopher Wayne Hardy, Coleambally (AU); Susan Robin Hardy, Coleambally (AU); Allan Rex Todd, Bell Post Hill (AU); Trent Martin Mohay, Ascot Vale (AU); Warren Ralph Deitch, Taradale (AU)

(73) Assignee: CW & SR INVESTMENTS PTY LTD, Coleambally (AU)

( * ) Notice: Subject to any disclaimer, the term of this patent is extended or adjusted under 35 U.S.C. 154(b) by 160 days.

(21) Appl. No.: 15/761,500

(22) PCT Filed: Sep. 21, 2016

(86) PCT No.: PCT/AU2016/000329
§ 371 (c)(1),
(2) Date: Mar. 20, 2018

(87) PCT Pub. No.: WO2017/049336
PCT Pub. Date: Mar. 30, 2017

(65) Prior Publication Data
US 2018/0259407 A1   Sep. 13, 2018

(30) Foreign Application Priority Data

Sep. 21, 2015   (AU) ................................. 2015903840

(51) Int. Cl.
*G01L 5/28*   (2006.01)
*B60T 17/22*   (2006.01)
(Continued)

(52) U.S. Cl.
CPC .................. *G01L 5/28* (2013.01); *A61B 5/18* (2013.01); *B60T 17/22* (2013.01); *G07C 5/08* (2013.01);
(Continued)

(58) Field of Classification Search
CPC .. G01L 5/28; G01L 5/225; A61B 5/18; A61B 5/162; A61B 2503/22; B60T 17/22;
(Continued)

(56) References Cited

U.S. PATENT DOCUMENTS

| 4,206,636 A * | 6/1980 | Hendrix | ................. G01L 1/2206 73/132 |
| 2007/0001831 A1* | 1/2007 | Raz | ..................... B60R 16/0231 340/439 |

(Continued)

FOREIGN PATENT DOCUMENTS

| AU | 2010241314 A1 | 5/2011 |
| GB | 2 159 111 A | 11/1985 |
| WO | WO 2014152802 | * 9/2014 |

OTHER PUBLICATIONS

International Search Report, PCT/AU2016/000329, dated Nov. 18, 2016 (4 pgs.).

(Continued)

*Primary Examiner* — Harshad R Patel
*Assistant Examiner* — Nigel H Plumb
(74) *Attorney, Agent, or Firm* — Eversheds Sutherland (US) LLP

(57) ABSTRACT

The present invention relates to testing and evaluation of motorised wheeled vehicles and the evaluation of drivers of motorised wheeled vehicles including a system for evaluation of driver braking performance. The system may include a driver measuring unit including a force measuring means being operative to generate force measurement data repre- (Continued)

sentative of force applied by the driver to the brake applicator and a communication means, a vehicle measuring unit having a motion measuring means adapted to determine vehicle measurements and a communication means, and a processor unit having a display screen, and communications means, wherein the processor unit is operative to receive via the communications means the force measurement data generated by the driver measuring unit and the vehicle measurement data generated by the vehicle measuring unit, and generate brake test result metrics therefrom for display on the display screen.

19 Claims, 9 Drawing Sheets

(51) Int. Cl.
| | |
|---|---|
| *G07C 5/08* | (2006.01) |
| *G09B 19/16* | (2006.01) |
| *A61B 5/18* | (2006.01) |
| *B60K 28/06* | (2006.01) |
| *G07C 5/00* | (2006.01) |
| *A61B 5/16* | (2006.01) |
| *G01L 5/22* | (2006.01) |

(52) U.S. Cl.
CPC ............ *G09B 19/167* (2013.01); *A61B 5/162* (2013.01); *A61B 2503/22* (2013.01); *B60K 28/06* (2013.01); *B60T 2210/36* (2013.01); *B60T 2220/02* (2013.01); *B60T 2270/406* (2013.01); *G01L 5/225* (2013.01); *G07C 5/008* (2013.01); *G07C 5/0816* (2013.01)

(58) Field of Classification Search
CPC ............ B60T 2210/36; B60T 2220/02; B60T 2270/406; G07C 5/08; G07C 5/008; G07C 5/0816; G09B 19/167; B60K 28/06
See application file for complete search history.

(56) References Cited

U.S. PATENT DOCUMENTS

2009/0070027 A1\* 3/2009 Newhouse ................ G01L 3/26
  701/123
2014/0272810 A1\* 9/2014 Fields ................ G01C 21/3676
  434/65

OTHER PUBLICATIONS

Written Opinion, PCT/AU2016/000329, dated Nov. 18, 2016 (5 pgs.).

\* cited by examiner

METHOD AND APPARATUS FOR EMERGENCY BRAKING PERFORMANCE TESTING, EVALUATION AND/OR DRIVER TRAINING

RELATED APPLICATIONS

This application claims priority to Australian Provisional Patent Application No. 2015903840 in the name of CW & SR Investments Pty Ltd, which was filed on 21 Sep. 2015, entitled "Method and Apparatus for Emergency Braking Performance Testing, Evaluation and/or Driver Training" and the specification thereof is incorporated herein by reference in its entirety and for all purposes.

FIELD OF INVENTION

The present invention relates to methods and apparatus for testing and evaluation of motorised wheeled vehicles and in particular, the testing, evaluation and training of drivers of motorised wheeled vehicles. It will be convenient to hereinafter describe the invention in relation to evaluation of road vehicle braking performance with respect to emergency braking performance, however it should be appreciated that the present invention is not limited to that use, only.

BACKGROUND ART

The discussion throughout this specification comes about due to the realisation of the inventor and/or the identification of certain related art problems by the inventor and, moreover, any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

Driving a motor vehicle on public roads is a complex task requiring many learned skills. One aspect of driving that can significantly influence road safety is the ability to effectively execute a braking manoeuvre under emergency conditions. Vehicular accidents can result from poor driver emergency braking skills. Yet, at present, there is a lack of metric(s)-based emergency stop training tools available for drivers.

Licencing compliance authorities do not require any form of metric(s)-based testing to achieve an understanding of a driver's ability to react effectively and efficiently in an emergency braking situation.

SUMMARY OF INVENTION

In a first aspect of embodiments described herein there is provided a system for evaluation of driver braking performance, comprising:

a driver measuring unit including a force measuring means and a communications means, the driver measuring unit being adapted for attachment to a road vehicle brake applicator interface and being operative to generate force measurement data representative of force applied by the driver to the brake pedal during an evaluation period and transmit the force measurement data using the communications means;

a vehicle measuring unit, in use carried by the vehicle, having a motion measuring means adapted to determine vehicle measurements comprising one or more of the vehicle acceleration, velocity and position, and a communications means, the vehicle measuring means being operative to generate vehicle measurement data during an evaluation period and transmit the vehicle measurement data using the communications means; and a processor unit having a display screen, and communications means, wherein the processor unit is operative to receive via the communications means the force measurement data generated by the driver measuring unit and the vehicle measurement data generated by the vehicle measuring unit, and generate one or more brake test result metrics therefrom for display on the display screen.

The force measuring means of the driver measuring unit may be adapted for temporary attachment to the brake applicator interface, which may be in the form of a brake pedal or a brake handle or lever.

The motion measuring means of the vehicle measuring unit may include a GPS receiver capable of determining the vehicle speed, distance travelled and/or path during the evaluation period. The motion measuring means may also include an accelerometer capable of determining vehicle acceleration during the evaluation period.

The communications means of the driver measuring unit, vehicle measuring unit and processor unit may comprise short-range wireless transceivers, for example Bluetooth Low Energy transceivers.

The processor unit may comprise a portable computing device, for example in the form of a smartphone or tablet computer.

The processor unit and/or the vehicle measuring unit may include means for issuing an audible signal to signify beginning of an evaluation period. This may be through an in-built audio emitter (e.g. speaker or buzzer) or through short range communications with the vehicle audio system, for example.

The processor unit may include a user interface that enables a user to input a desired vehicle test commencement speed. The system may be operative to issue an audible signal following the vehicle reaching the test commencement speed as determined by the motion measuring means. The system may also or alternatively be operative to issue an audible signal upon a user command. The audible signal may be issued by the processor unit or the vehicle measuring unit, or under control of either one through an audio system of the vehicle.

The processor unit may be operative to determine a driver reaction time based on the timing of the audible signal and force measurement data received from the driver measuring unit.

The system may further include an internet based evaluation unit adapted to receive brake test result metrics from the processor unit by way of internet communications, for comparison of collected results from different tests and evaluation against predetermined criteria. The processor unit (e.g. smart-phone) may transmit data to a web site with the ability to log successive testing sessions with other relevant information and rank against industry standards and other users and with potential to export collated data to relevant authorities, and may also have the capability to accurately log and print all measurement data for the purpose of determining a pass or fail result for licence compliance.

In a second aspect of embodiments herein there is provided a method of evaluating driver braking performance, comprising the steps of:

collecting force measurement data representative of force applied by the driver to the brake pedal of a vehicle during an evaluation period;

collecting vehicle measurements comprising one or more of the vehicle acceleration, velocity and position during the evaluation period;

communicating force measurement data and vehicle measurement data collected during the evaluation period to a processor unit having a display screen, wherein the processor unit is operative to receive the force measurement data and the vehicle measurement data and generate one or more brake test result metrics therefrom for display on the display screen.

In another aspect of embodiments described herein there is provided a method for evaluation of driver braking performance, comprising:

equipping a vehicle with a driver measuring unit including a force measuring means adapted for attachment to a road vehicle brake applicator interface and being operative to generate force measurement data representative of force applied by the driver to the brake pedal during an evaluation period;

equipping the vehicle with a vehicle measuring unit having a motion measuring means adapted to determine vehicle measurements comprising one or more of the vehicle acceleration, velocity and position, the vehicle measuring means being operative to generate vehicle measurement data during the evaluation period;

communicating force measurement data and vehicle measurement data collected during the evaluation period to a processor unit having a display screen, wherein the processor unit is operative to receive the force measurement data generated by the driver measuring unit and the vehicle measurement data generated by the vehicle measuring unit, and generate brake test result metrics therefrom for display on the display screen.

The method may include issuing a test commencement signal under control of one of the processor unit and the vehicle measuring unit, such as an audible or visual signal discernible by the vehicle driver. The test commencement signal may be issued once the vehicle, as determined by the motion measuring means, reaches a predetermined test commencement speed.

The brake test result metrics generated by the processor unit may include a driver reaction time determined based on the timing of the test commencement signal and force measurement data received from the driver measuring unit.

The brake test result metrics may be communicated to an internet based evaluation unit for comparison of collected results from different tests and evaluation against predetermined criteria. The internet based evaluation unit may be in the form of a web site with the ability to log successive testing sessions with other relevant information and rank against industry standards and other users and with potential to export collated data to relevant authorities, and may also have the capability to accurately log and print all measurement data for the purpose of determining a pass or fail result for licence compliance.

Preferred embodiments of the invention are directed to the generation of brake result metrics to be used in evaluation of driver braking performance for display in a user or vehicle carried product, the brake result metrics provided by force measurement data generated by a driver measuring unit adapted for attachment to a road vehicle brake applicator interface and vehicle measurement data generated by a vehicle measuring unit having a motion measuring means adapted to determine vehicle measurements comprising one or more of the vehicle acceleration, velocity and position, and communications means with a processor unit for the display.

Other aspects and preferred forms are disclosed in the specification and/or defined in the appended claims, forming a part of the description of the invention.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

The invention may be better understood by those skilled in the relevant art from the following description of embodiments thereof, provided by way of example only, and taken in conjunction with the accompanying drawings, in which.

DETAILED DESCRIPTION

Devices, apparatus, systems and processes forming embodiments of the invention are described below. The general purpose of the system is to enable quantifiable testing and evaluation of braking performance of drivers and vehicles in real-world road driving conditions, particularly when required to execute an emergency stop. The system and processes can be used to assist in driver training and may therefore find use during instruction of learner drivers and the like.

Figure 1:
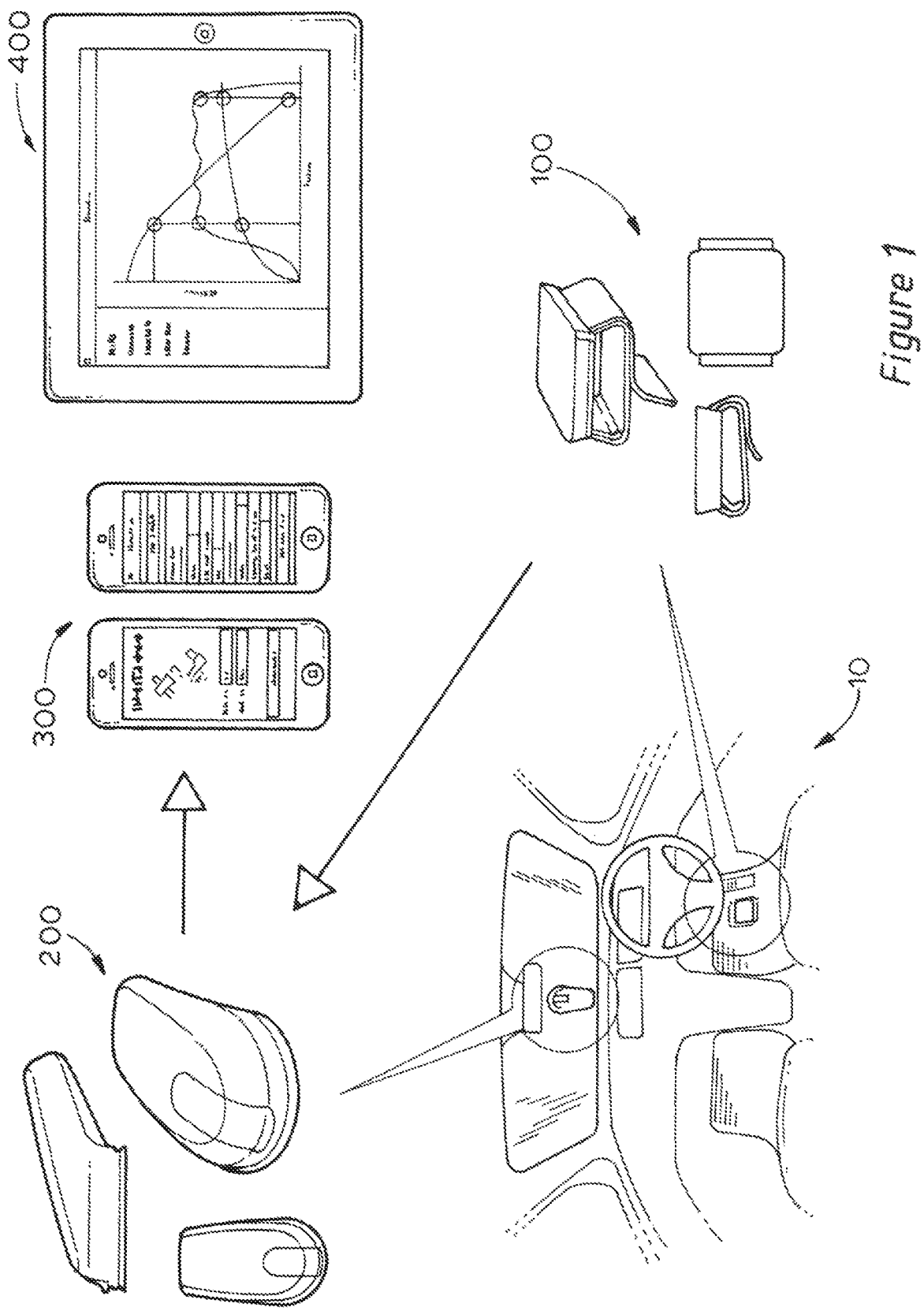
FIG. 1 is a conceptual system diagram illustrating an embodiment of the invention.

A conceptual system diagram of an embodiment of the invention is shown in FIG. 1. The system 10 comprises several units that communicate and operate together to provide the functionality as described herein. A pedal force sensor (PFS) unit 100 is provided to measure the force applied by the driver to the vehicle brake pedal during use of the system. A vehicle motion sensing (VMS) unit 200 is provided to measure motion of the vehicle during use of the system, which may include position, velocity and/or acceleration (for the purposes of this description the term "acceleration" is used in a general sense to refer to change in velocity of the vehicle, and thus encompasses "deceleration" through vehicle braking). A processor unit 300 is provided to coordinate the system and receive measurement data from the VMS and PFS during use, process the received data and provide visual display output therefrom. In the preferred form of the invention the PFS, VMS and processor unit are all carried by the vehicle during use of the system. A further, web-based, analysis tool 400 may also be provided for post-analysis and comparison of results from other drivers, vehicles, manufactures, etc.

Figure 2:
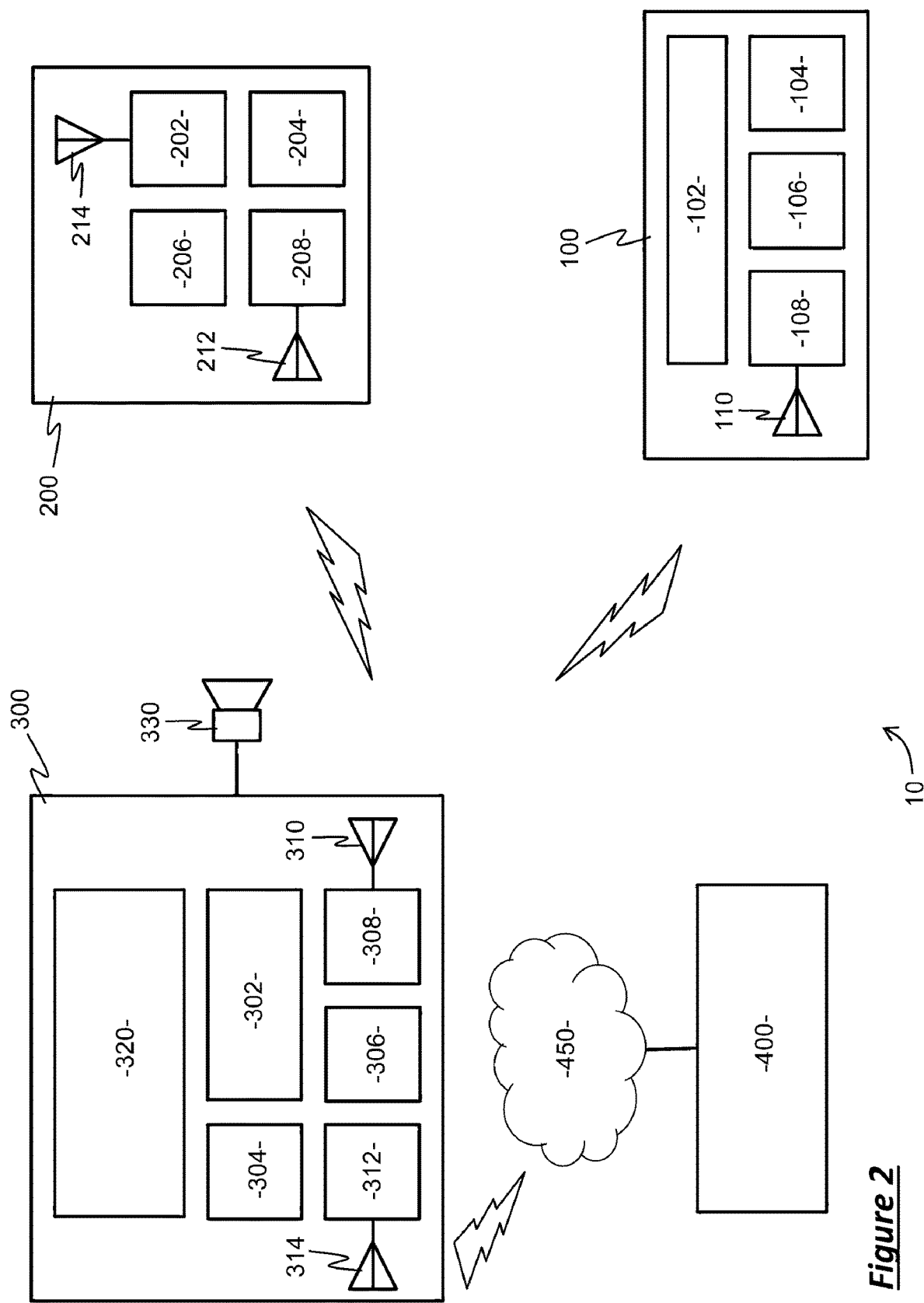
FIG. 2 is a functional block diagram of an embodiment of the invention.

FIG. 2 is a functional block diagram of the system 10 illustrating the functional components in greater detail.

The PFS unit 100 includes a force sensitive load cell 102, control circuitry 106, a power supply unit 104, and communications circuitry 108.

The load cell 102 is a transducer that is used to create an electrical signal whose magnitude is directly proportional to the force being measured. In this case, as explained further hereinbelow, the force of interest is that applied by the driver's foot to the brake pedal of the vehicle. The load cell may be of any convenient type, such as a strain gauge or piezoelectric transducer.

The control circuitry 106 is coupled to receive output from the load cell 102 representative of forces measured. The control circuitry may include amplification circuitry, analogue-to-digital conversion circuitry, and general processing capability. A form of integrated circuit microcontroller may be employed for this purpose. In use the control circuitry digitizes force measurement signals from the load cell.

The communications circuitry 108 is for short-range wireless communication and may comprise, for example, a Bluetooth standard transceiver. A preferred form of communications circuit operates according to the Bluetooth low-energy (BLE) specification in order to minimize electrical power usage. The communications circuitry is coupled to the control circuitry for the purpose of transmitting, using an antenna 110, the digital force measurement signals.

The embodiment described herein employs short-range wireless communications in the form of BLE transceivers because it is convenient insofar as physical connections between units are not required. However it is also possible to implement the system using wires for communication between the PFS, VMS and/or processor unit, in which case the control circuitry and the form of the signals therebetween may differ. Whilst a hardwired embodiment of the system may be less convenient to install in a vehicle, improved timing accuracy may be achieved through avoidance of wireless protocol transmission latency.

The power supply unit (PSU) 104 provides electrical power to the load cell, control circuitry and communications circuitry. The power supply is preferably self-contained, including a battery. The battery may be in the form of a lithium-polymer rechargeable battery, for example, which has high energy-density by weight.

Figure 3:
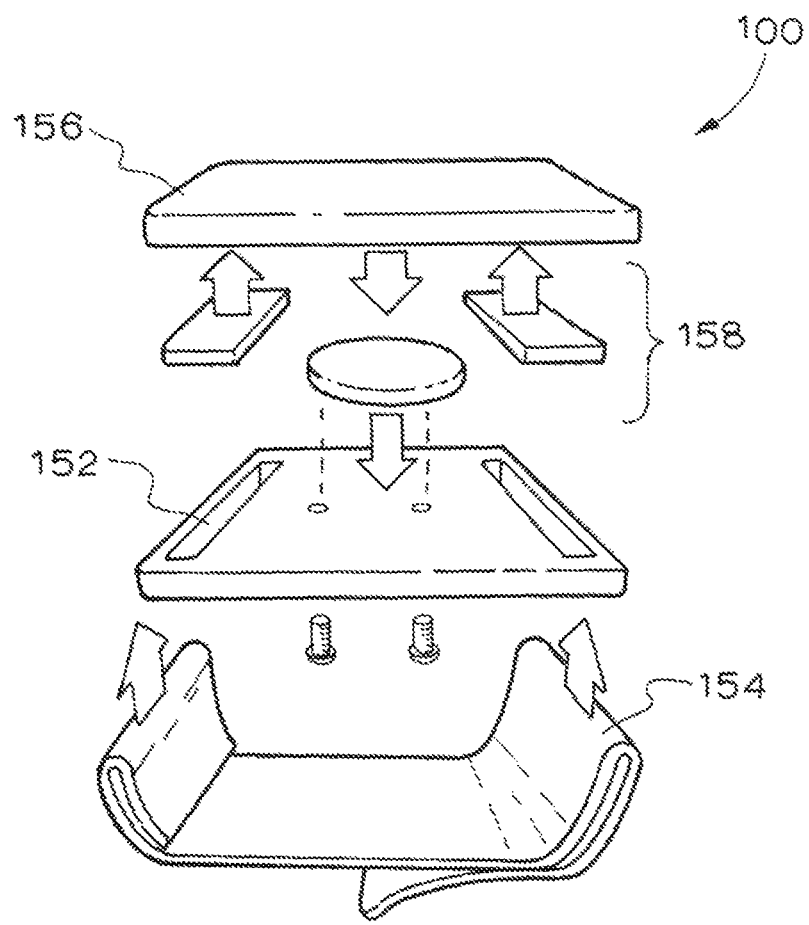
FIG. 3 is an exploded diagram illustrating features of a brake pedal force sensing unit from an embodiment of the invention.

An exploded diagram illustrating features of an exemplary brake pedal force sensing unit 100 is shown in FIG. 3. The diagram illustrates an indicative structure which includes a base plate 152 and fastening strap 154. The base plate is adapted to be positioned on the foot engaging surface of a vehicle brake pedal. The fastening strap is coupled to the base plate and is adapted to pass around the underside of the brake pedal and be tightened to securely fasten the PFS unit to the brake pedal, in use. The PFS unit 100 also includes a foot plate 156 which couples to the base plate, housing the operative components 158 (i.e. power supply, load cell, control and communications circuits) therebetween.

When the PFS unit 100 is secured to the pedal it acts as an interface between the driver's foot and the vehicle brake pedal. Thus, when the driver applies the brake the driver's foot engages the top surface of the foot plate 156 and force is transmitted through the PFS unit to the brake pedal. Accordingly, the top surface of the foot plate 156 may be rubberized, textured and/or otherwise treated to have a non-slip characteristic. The coupling between the foot plate and the base plate is such that forces applied by the driver's foot, and transferred to the brake pedal, can be sensed and measured by the load cell mounted therebetween. To avoid interference with the driver's foot the PFS should have a slim form factor.

The vehicle motion sensing (VMS) unit 200 includes motion sensing circuitry 202, control circuitry 206, a power supply unit 204, and communications circuitry 208.

The motion sensing circuitry 202 is provided to measure characteristics of the vehicle motion, in use. In particular, the motion sensing circuitry provides the VMS unit with the capability of determining the vehicle acceleration, speed, and/or location. In order to accomplish this, the motion sensing circuitry may include an inertial measurement unit (IMU) and/or a global positioning system (GPS) receiver. There are several different methods by which such components may be employed in embodiments of the invention.

A first measurement method employs direct deceleration measurements based on 3-axis accelerometer (IMU). In this case deceleration measurements, to national standards, are possible at relatively low cost, with high accuracy deceleration metrics possible at elevated cost. If used in isolation, however, double integration calculations would be required to derive distance metrics, and accumulative errors resulting therefrom may result in mean distance metrics being of indicative quality only.

A second measurement method determines distance measurements based on differential GPS (DGPS) positioning using real-time kinematic (RTK) techniques over Ntrip ('Networked Transport of RTCM via Internet Protocol'). This can provide highly accurate positional measurements to centimetre accuracy. However, double integration calculations would be required to derive deceleration rates, reducing accuracy in that metric. Depending on geographic location, an Ntrip subscription may be required, impacting on implementation costs.

A third measurement method determines velocity measurements based on the Doppler-effect on a GPS L1 carrier signal. This emerging technology promises precise velocity measurements, which would then enable single-step, calculated integration to determine deceleration and/or distance metrics.

The motion sensing circuitry 202, in a currently preferred form of the VMS unit 200, uses a GPS receiver in conjunction with an inertia measurement unit to measure the vehicle motion characteristics, in use. For example, a 10 Hz SBAS (satellite-based augmentation system) enable GPS receiver may be employed for vehicle position tracking and speed determination. Additionally, an IMU may be employed for vehicle deceleration measurement and measurement compensation. An accelerometer range of +/−2 g should be generally sufficient, with deceleration calculations of 5% (3% MFDD) accuracy or better preferred.

The VMS control circuitry 206 is coupled to receive output from the motion sensing circuitry 202 representing measured vehicle motion characteristics (i.e. vehicle position, speed, acceleration). The control circuitry may include interface circuitry, analogue-to-digital conversion circuitry, and general processing capability. A form of integrated circuit microcontroller may be employed for this purpose.

The VMS communications circuitry 208 is for short-range wireless communication and may comprise, for example, a Bluetooth standard transceiver. A preferred form of communications circuit operates according to the Bluetooth low-energy (BLE) specification in order to minimize electrical power usage. The communications circuitry is coupled to the control circuitry for the purpose of transmitting, using an antenna 210, the measured vehicle motion characteristics. As explained hereinabove, the VMS may alternatively communicate with the PFS and/or processor unit through wired coupling rather than wireless communications if desired.

The power supply unit (PSU) 204 provides electrical power to the motion measurement circuitry, control circuitry and communications circuitry. The power supply is preferably self-contained, including a battery. The battery may be in the form of a lithium-polymer rechargeable battery, for example, which has high energy-density by weight.

To allow for reliable reception of GPS signals the VMS unit may be, in use, mounted to the vehicle windscreen, dashboard or other GPS accessible location (even on the outside of the vehicle if necessary).

The function of the processor unit 300 is to receive measurement data signals from the PFS unit 100 and VMS unit 200 for processing, analysis and display. The processor unit 300 includes a processor and memory/data-storage (302, 304), a power supply unit 306, short-range wireless communication circuitry and antenna (308, 310), cellular and/or Wi-Fi communications and antenna (312, 314), and a graphical display screen 320. The processor unit may also include or be coupled to an audible emitter 330, such as an audio speaker, alarm beeper or the like. The functions of the processor unit 300 may be provided by a smartphone, tablet computer or similar, acting under control of an application software program to provide the operations described herein.

Figure 4:
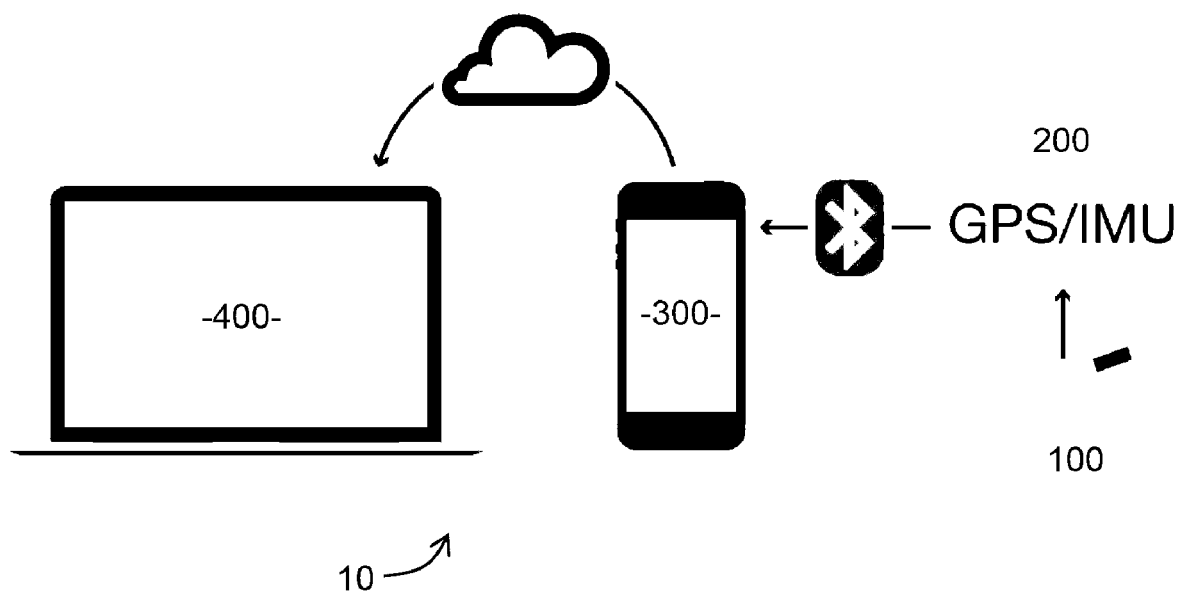
FIG. 4 is an annotated system diagram of an embodiment of the invention.
Figure 5:
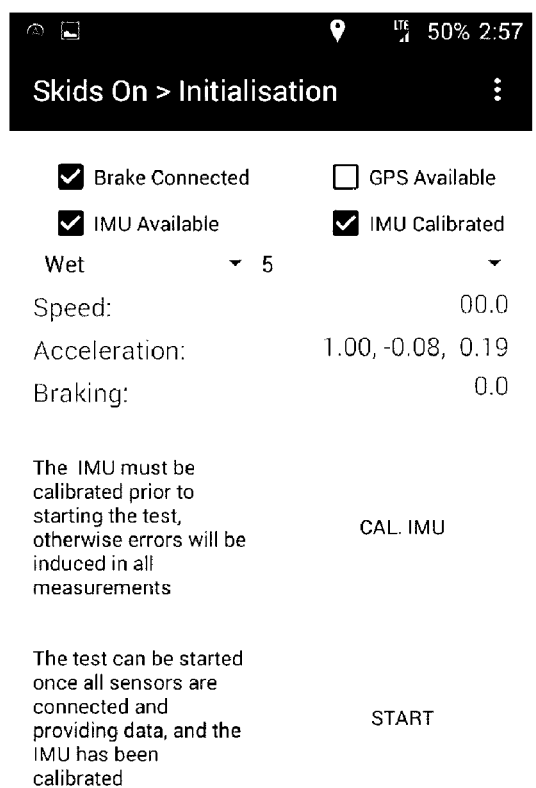
FIG. 5 is a screen-shot representation from a processor unit software user interface used in an embodiment of the invention.

FIG. 4 is an annotated system diagram illustrating the primary functional units of the system 10. The brake pedal force sensor 100 is used to capture pedal application behaviour and provide a timing trigger, and is coupled to the VMS unit 200 by way of Bluetooth and/or wired connection. The VMS unit 200 includes one or more accelerometer or IMU/INS and GPS device for capturing vehicle deceleration and velocity data. Data from the VMS unit is communicated through a Bluetooth communications connection to the processor unit 300 which may comprise a standalone and/or Internet-of-Things (IoT) connected smart device running an App supporting system setup, device calibration, test evaluation and IoT connectivity. The processor unit 300 may utilise cellular data internet communications to transfer test results data to analysis computer 400 operating web-based analytical software and providing a temporary data storage facility. The analysis computer 400 can be used for post-analysis of the test results data and comparison of results with other instances, users, vehicle types, vehicle manufacturers, etc.

In use of the system 10, the processor unit 300 acts to provide signals to the driver during a testing procedure, and the driver acts upon those signals. The processor unit receives and stores motion and brake force measurements from the PFS unit 100 and VMS unit 200, stores and analyses the measurement data, and provides graphical display output of the test performance. In the interests of safety, the system is preferably operated under control of an instructor who is a passenger in the vehicle. An example of a testing procedure using the system 10 in accordance with an embodiment of the invention is illustrated in flow diagram form in FIG. 6 and explained below.

Figure 6:
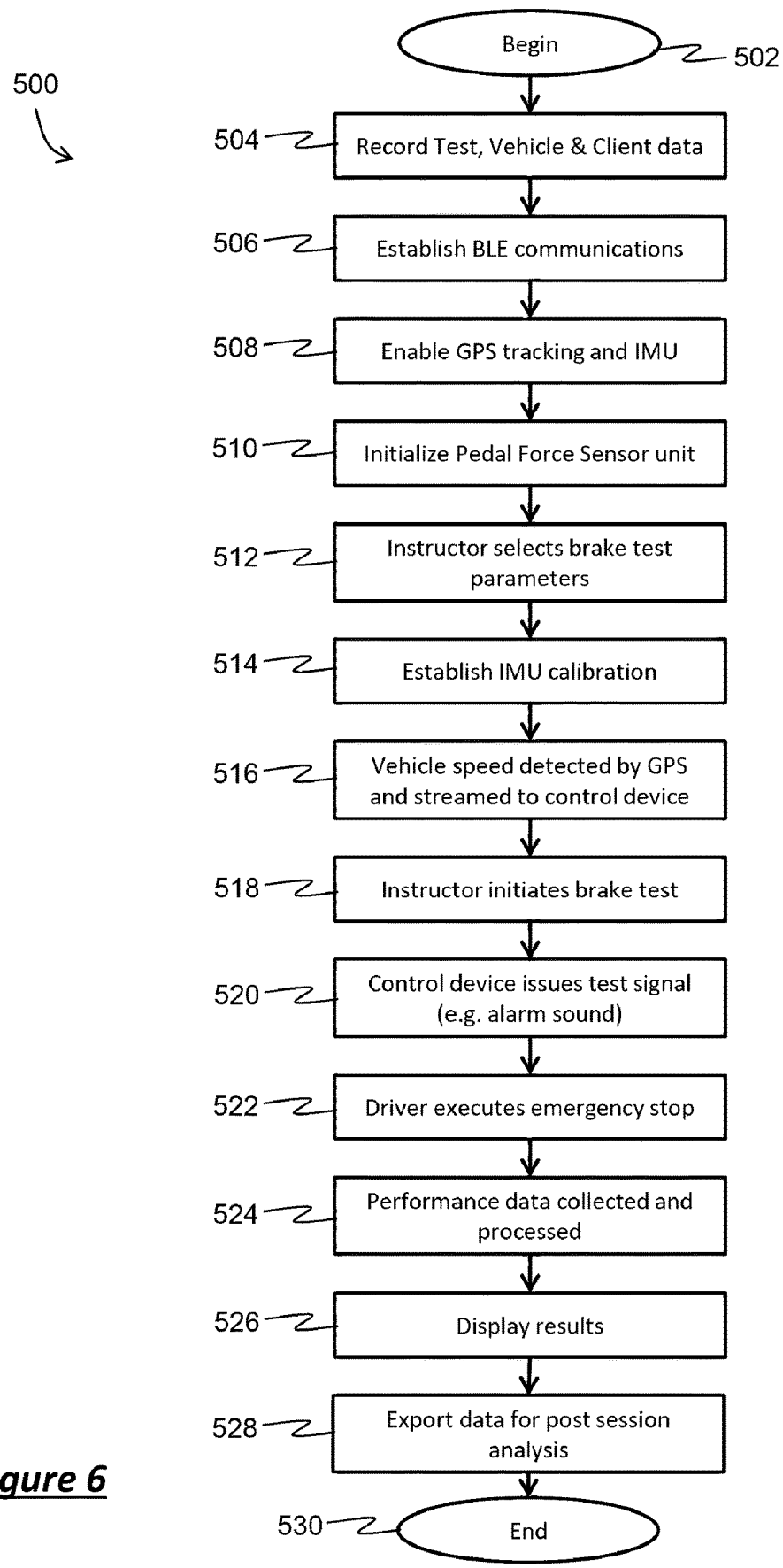
FIG. 6 is a flow chart diagram illustrating a procedure according to an embodiment of the invention.

A vehicle brake performance testing procedure 500 which may be performed utilising a system 10 as described herein is shown as a sequence of operations in FIG. 6, beginning at 502. The procedure 500 is performed through use of a vehicle fitted with the system 10, a driver in control of the vehicle, and an instructor, being a passenger in the vehicle, in control of the processor unit.

Initially, the instructor uses the processor unit to record identification data (504), such as the nature of the test to be completed, the vehicle and the driver. Then, prior to commencement of the test, the processor unit is operative to establish wireless communications (506) with the PFS unit and the VMS unit. Through the wireless communication link (e.g. BLE) the processor unit instructs the VMS unit to enable GPS tracking and IMU measurements (508), and instructs the PFS unit to initialize force sensing measurements (510).

At operation 512 the instructor uses the processor unit application interface to select the brake test parameters. This may include, for example, the desired vehicle speed from which braking is to commence. Where necessary, IMU calibration is established (514).

The vehicle driver then accelerates the vehicle to the predetermined speed, whilst data representing the vehicle speed and location as determined by the GPS is streamed from the VMS to the processor unit (516). When the vehicle has reached the predetermined speed the instructor, through the processor unit interface, initiates the brake test (518). Alternatively, the processor unit may initiate the brake test automatically once the predetermined vehicle speed has been reached.

An audible test signal (e.g. and alarm sound) is issued by the processor unit (520) to signify to the driver to brake the vehicle to a stop. When the driver hears the test signal he or she executes an emergency stop (522) using the vehicle brake pedal fitted with the PFS unit. During this time measurements from the VMS and PFS are collected and transmitted to the processor unit (524). The vehicle position, speed and acceleration data received from the VMS unit and the brake force data received from the PFS unit are stored in time series by the processor unit.

Once the vehicle has been brought to a stop, the test run is complete and the instructor may then use the processor unit to display test results to the driver (528). The test results data may also be uploaded through cellular or wireless network (Wi-Fi) communications to a web-based portal (400 in FIG. 2) for further analysis and comparison against test results from other drivers and vehicles.

Figure 7:
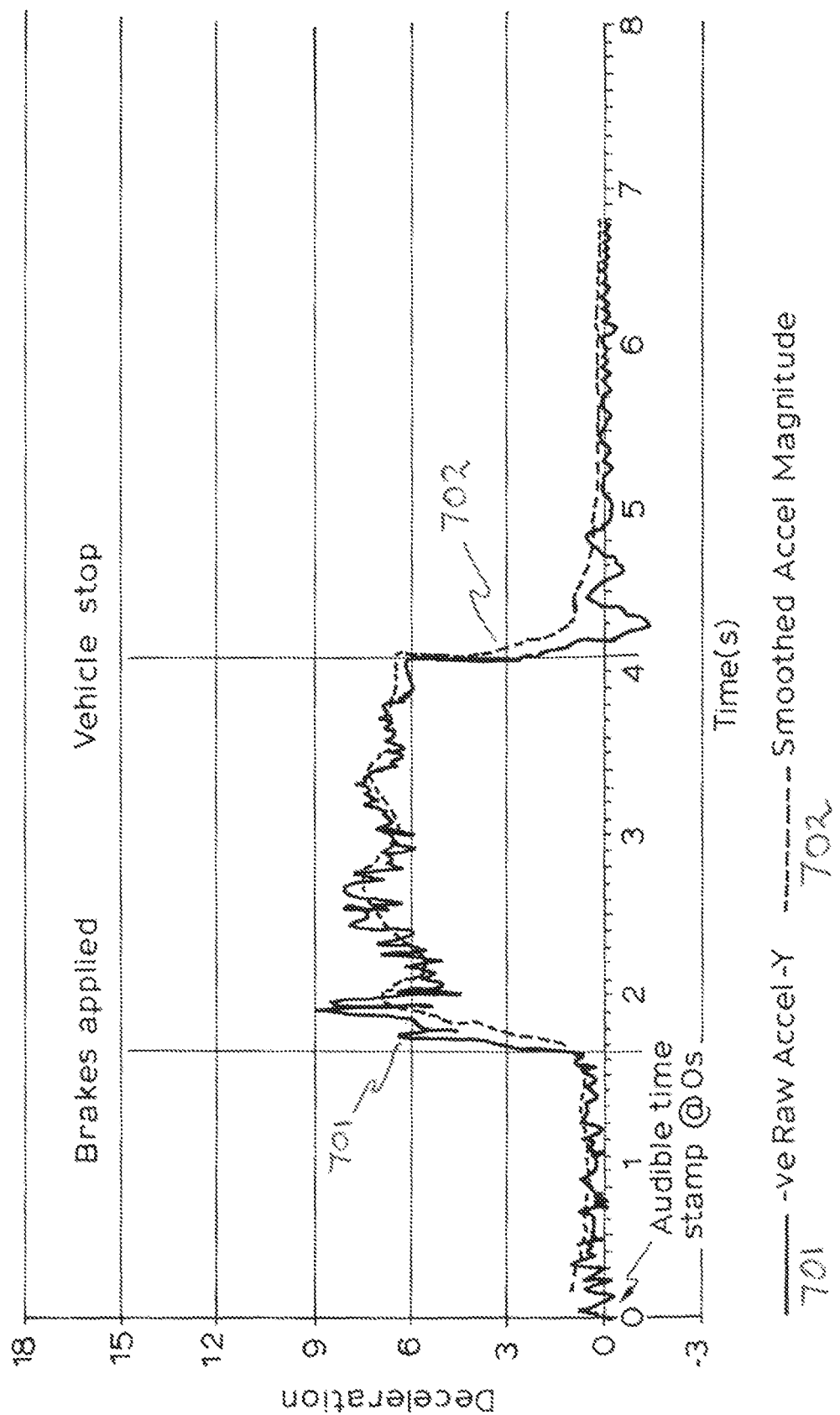
FIGS. 7, 8 and 9 are graphical diagrams illustrating analysis of results according to an embodiment of the invention.
Figure 8:
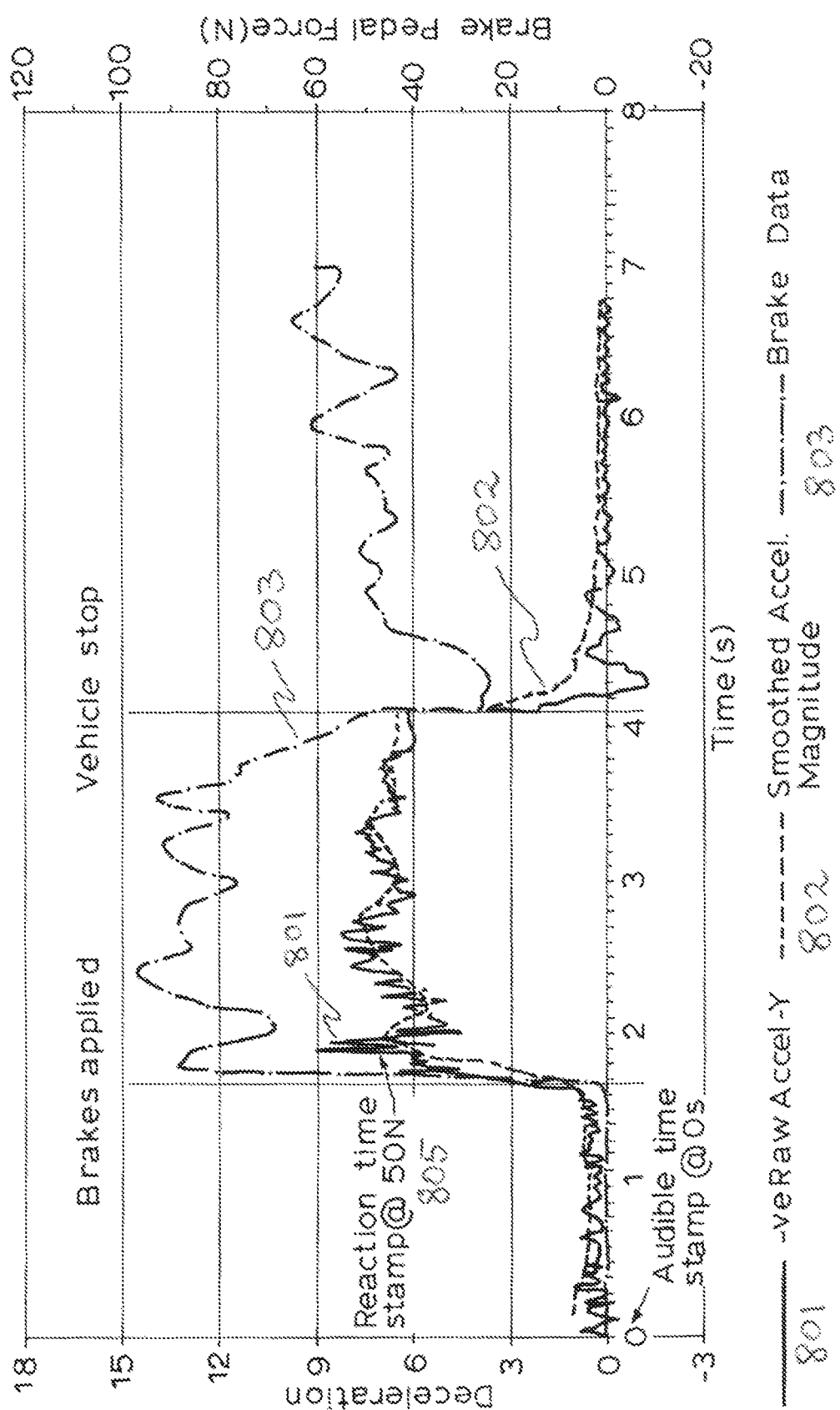
Figure 9:
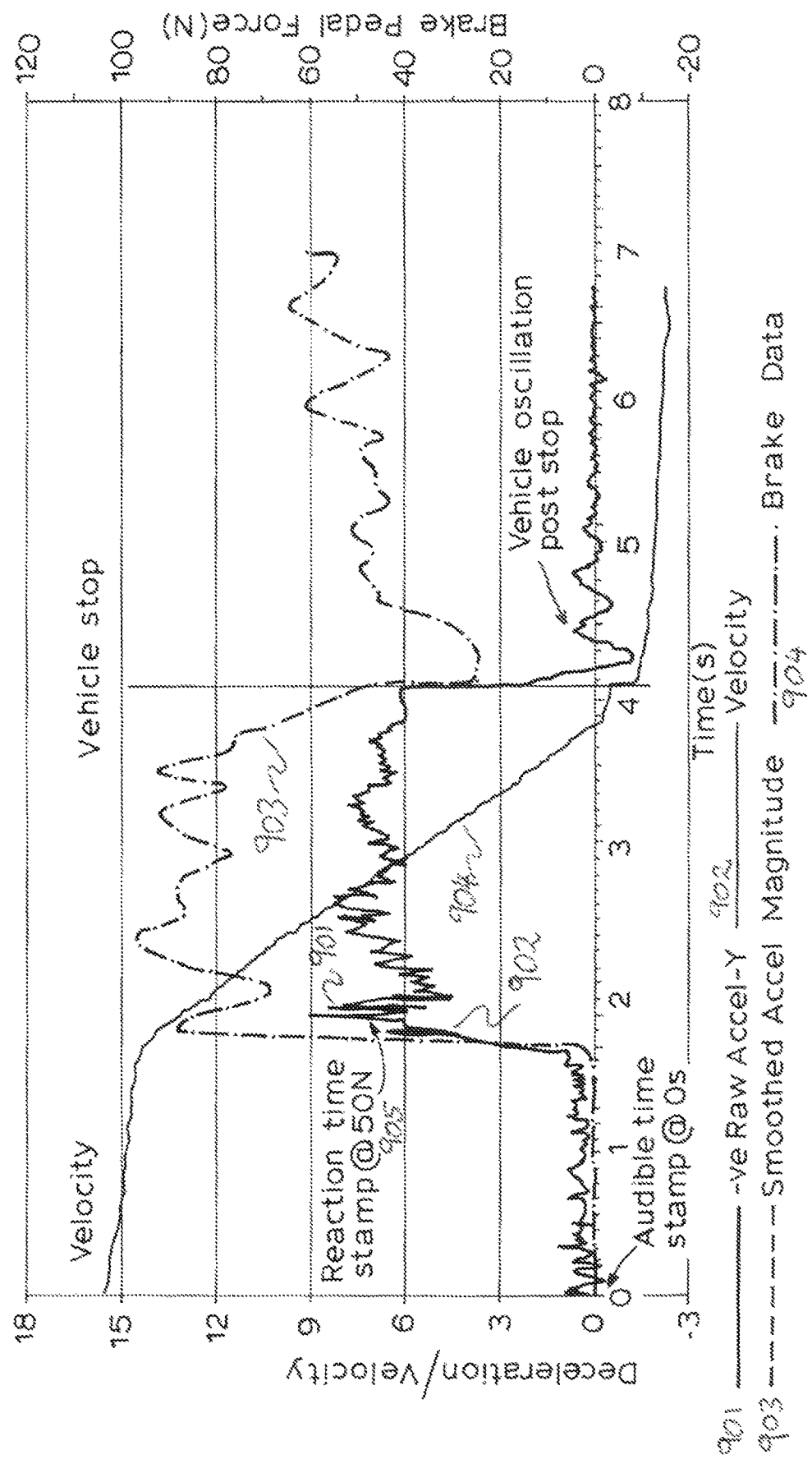

Using the measurement data collected from the VMS and PFS units the processor unit is able to determine a number of metrics representing the results of the brake testing procedure. Relevant metrics may include such things as driver reaction time, vehicle stop time, vehicle stop distance, etc. The processor unit may also present the collected measurement data in one or more graphical representations. FIGS. 7, 8 and 9 are examples of graphical representations illustrating test results that may be displayed by the processor unit following completion of a test run. FIG. 7 shows a plot of IMU derived vehicle acceleration over a time period of the test, beginning at the time the processor unit issues the audible test signal. For the purposes of illustration both the raw vehicle acceleration data plot (701, 801, 901) and smoothed data plot (702, 802, 902) are shown. FIGS. 8 and 9 additionally show a plot of the brake pedal force data (803, 903) during the test procedure time period. FIG. 9 additionally shows a plot (904) of vehicle speed during the test procedure time period.

Referring to FIG. 8 in particular, the driver reaction time and vehicle stop time can be readily discerned from the graph. The driver reaction time is the time period from the test period start (i.e. when the processor unit issues an audible test signal) to the point at which the driver begins to apply the vehicle brakes. The reaction time stamp, as indicated at 805 in FIG. 8, it determined when the force applied to the brake pedal reaches a predetermined level (50N in this example). The point at which the vehicle comes to a stop can be readily determined from the acceleration measurement data (in conjunction with the brake pedal force data) and/or the speed measurement data.

Figure 10:
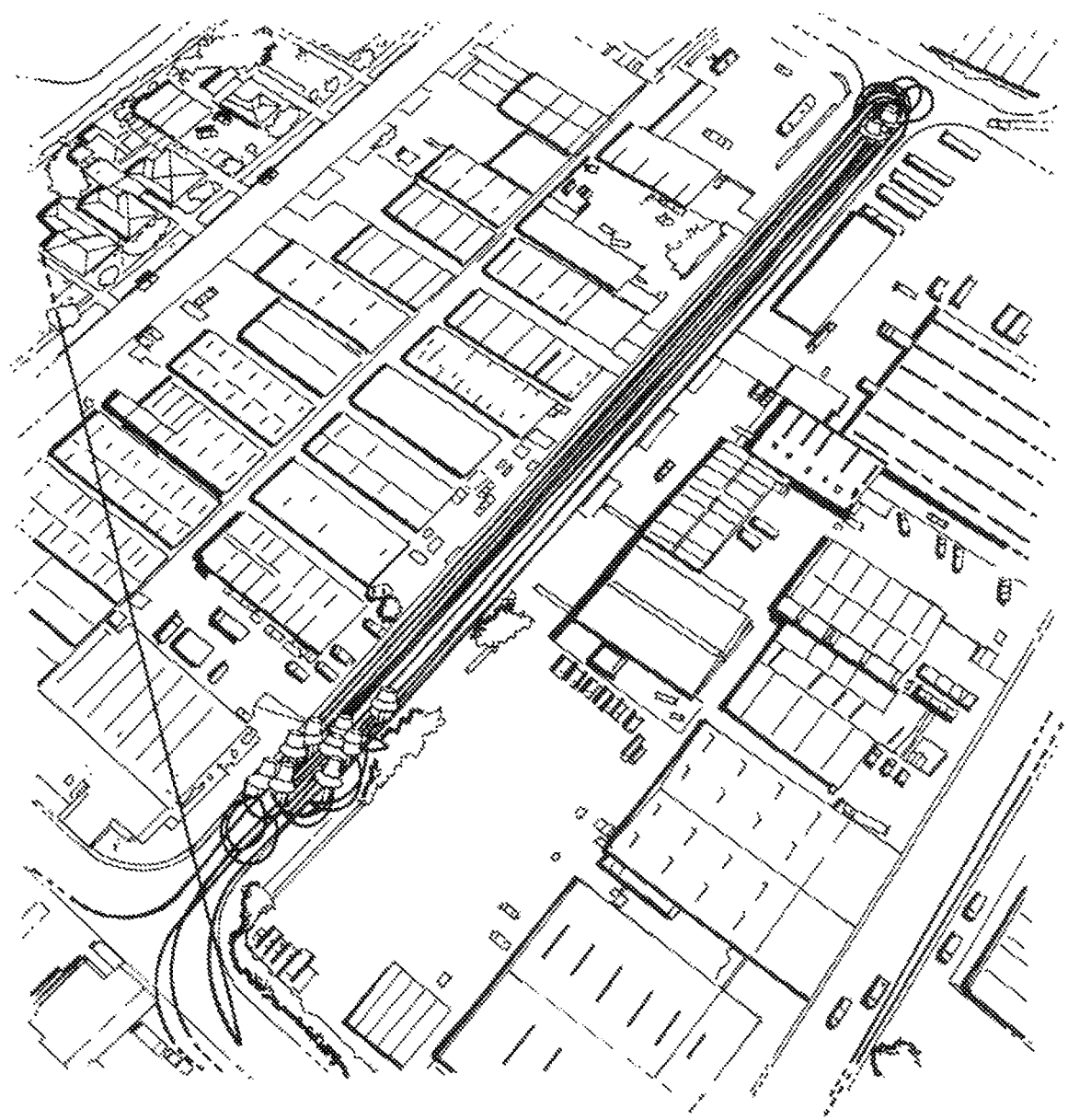
FIG. 10 is a screen-shot representation of a vehicle location display that may be employed in embodiments of the invention.

Using the location data obtained from the GPS receiver, the processor unit may also provide the user with graphic overlay displayed on mapping or aerial imagery, providing a record of the brake test location and path, which may also indicate the location of the vehicle at each of the significant test time points (e.g. test start, brakes first applied, vehicle stop, etc.). FIG. 10 illustrates an example of vehicle path graphical overlay on aerial imagery during a series of test runs.

In the embodiment as described hereinabove, the PFS and VMS are configured to both communicate their respective data to the processor unit, however other arrangements are also possible. For example, the system may alternatively be configured whereby data from the PFS is communicated to the VMS rather than directly to the processor unit. This arrangement may provide improved measurement accuracy. In such a case the VMS may receive and store measurement data from the PFS during a testing period, and then provide the complete data set to the processor unit following completion of the test. During the test, the VMS may collate movement data and receive/interleave the PFS data. At the end of the test the VMS may push the complete data set to the processor unit.

The foregoing describes a system and method that may be used for capturing driver reaction time and braking performance data for the purpose of evaluating and improving a driver's overall emergency braking ability. The system may support electronic recording of learner driver practice logs and output these to relevant vehicle licensing authorities if desirable. Embodiments of the invention may find use in learner and advanced driving schools (for both passenger and heavy vehicles), as well as learner drivers and their supervisors (e.g. parents). The system and method may be used to test and improve all drivers' emergency braking skills, but may also be used in fleet management/service and vehicle inspection and compliance.

The system and method of the invention may be applied to various forms of vehicles including cars, trucks, vans, busses, RVs and the like, as well as vehicles such as bicycles, tricycles, motorcycles, scooters and the like. Thus, although the term 'driver' has been used throughout the specification to refer to the person in control of the vehicle during the testing procedure, that term will be understood to encompass the 'rider' of a vehicle where such reference is appropriate.

Whilst the primary embodiments described employ three main functional units—the PFS, the VMS and the processor unit—it is also possible to achieve results using a simpler system, although the accuracy will generally be inferior. One simple implementation may employ a single unit, carried by the vehicle, which performs the functions of both the above described processor unit and vehicle measuring unit. For example, a smartphone or tablet computer that incorporates a GPS receiver and/or accelerometer may be used to perform the VMS functions as well as process the data generated thereby during a test period. Evaluation metrics such as driver response time, in this instance, may be estimated from the vehicle motion data rather than actual data from a brake pedal sensor. However, the GPS and accelerometer sensors incorporated in such devices may lack sufficient accuracy and/or sensitivity to provide adequate measurement results.

The following sections I-VI provide a guide to interpreting the present specification.

I. Terms

The term "product" means any machine, manufacture and/or composition of matter, unless expressly specified otherwise.

The term "process" means any process, algorithm, method or the like, unless expressly specified otherwise.

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

The term "invention" and the like mean "the one or more inventions disclosed in this specification", unless expressly specified otherwise.

The terms "an embodiment", "embodiment", "embodiments", "the embodiment", "the embodiments", "one or more embodiments", "some embodiments", "certain embodiments", "one embodiment", "another embodiment" and the like mean "one or more (but not all) embodiments of the disclosed invention(s)", unless expressly specified otherwise.

The term "variation" of an invention means an embodiment of the invention, unless expressly specified otherwise.

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present specification, including anything which may be incorporated by reference", unless expressly specified otherwise.

The phrase "at least one of", when such phrase modifies a plurality of things (such as an enumerated list of things), means any combination of one or more of those things, unless expressly specified otherwise. For example, the phrase "at least one of a widget, a car and a wheel" means either (i) a widget, (ii) a car, (iii) a wheel, (iv) a widget and a car, (v) a widget and a wheel, (vi) a car and a wheel, or (vii) a widget, a car and a wheel. The phrase "at least one of", when such phrase modifies a plurality of things, does not mean "one of each of" the plurality of things.

Numerical terms such as "one", "two", etc. when used as cardinal numbers to indicate quantity of something (e.g., one widget, two widgets), mean the quantity indicated by that numerical term, but do not mean at least the quantity indicated by that numerical term. For example, the phrase "one widget" does not mean "at least one widget", and therefore the phrase "one widget" does not cover, e.g., two widgets.

The phrase "based on" does not mean "based only on", unless expressly specified otherwise. In other words, the phrase "based on" describes both "based only on" and "based at least on". The phrase "based at least on" is equivalent to the phrase "based at least in part on".

The term "represent" and like terms are not exclusive, unless expressly specified otherwise. For example, the term "represents" do not mean "represents only", unless expressly specified otherwise. In other words, the phrase "the data represents a credit card number" describes both "the data represents only a credit card number" and "the data represents a credit card number and the data also represents something else".

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The term "e.g." and like terms mean "for example", and thus does not limit the term or phrase it explains. For example, in the sentence "the computer sends data (e.g., instructions, a data structure) over the Internet", the term "e.g." explains that "instructions" are an example of "data" that the computer may send over the Internet, and also explains that "a data structure" is an example of "data" that the computer may send over the Internet. However, both "instructions" and "a data structure" are merely examples of "data", and other things besides "instructions" and "a data structure" can be "data".

The term "i.e." and like terms mean "that is", and thus limits the term or phrase it explains. For example, in the sentence "the computer sends data (i.e., instructions) over the Internet", the term "i.e." explains that "instructions" are the "data" that the computer sends over the Internet.

Any given numerical range shall include whole and fractions of numbers within the range. For example, the range "1 to 10" shall be interpreted to specifically include whole numbers between 1 and 10 (e.g., 2, 3, 4, . . . 9) and non-whole numbers (e.g., 1.1, 1.2, . . . 1.9).

II. Determining

The term "determining" and grammatical variants thereof (e.g., to determine a price, determining a value, determine an object which meets a certain criterion) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing, and the like.

The term "determining" does not imply certainty or absolute precision, and therefore "determining" can include estimating, extrapolating, predicting, guessing and the like.

The term "determining" does not imply that mathematical processing must be performed, and does not imply that numerical methods must be used, and does not imply that an algorithm or process is used.

The term "determining" does not imply that any particular device must be used. For example, a computer need not necessarily perform the determining.

III. Indication

The term "indication" is used in an extremely broad sense. The term "indication" may, among other things, encompass a sign, symptom, or token of something else.

The term "indication" may be used to refer to any indicia and/or other information indicative of or associated with a subject, item, entity, and/or other object and/or idea.

As used herein, the phrases "information indicative of" and "indicia" may be used to refer to any information that represents, describes, and/or is otherwise associated with a related entity, subject, or object.

Indicia of information may include, for example, a code, a reference, a link, a signal, an identifier, and/or any combination thereof and/or any other informative representation associated with the information.

In some embodiments, indicia of information (or indicative of the information) may be or include the information itself and/or any portion or component of the information. In some embodiments, an indication may include a request, a solicitation, a broadcast, and/or any other form of information gathering and/or dissemination.

IV. Forms of Sentences

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device or article is described herein, more than one device/article (whether or not they cooperate) may alternatively be used in place of the single device/article that is described. Accordingly, the functionality that is described as being possessed by a device may alternatively be possessed by more than one device/article (whether or not they cooperate).

Similarly, where more than one device or article is described herein (whether or not they cooperate), a single device/article may alternatively be used in place of the more than one device or article that is described. For example, a plurality of computer-based devices may be substituted with a single computer-based device. Accordingly, the various functionality that is described as being possessed by more than one device or article may alternatively be possessed by a single device/article.

The functionality and/or the features of a single device that is described may be alternatively embodied by one or more other devices which are described but are not explicitly described as having such functionality/features. Thus, other embodiments need not include the described device itself, but rather can include the one or more other devices which would, in those other embodiments, have such functionality/features.

V. Disclosed Examples and Terminology are not Limiting

Neither the Title nor the Abstract in this specification is intended to be taken as limiting in any way as the scope of the disclosed invention(s). The title and headings of sections provided in the specification are for convenience only, and are not to be taken as limiting the disclosure in any way.

Numerous embodiments are described in the present application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is not a literal description of all embodiments of the invention(s). Also, the present disclosure is not a listing of features of the invention(s) which must be present in all embodiments.

Devices that are described as in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for long period of time (e.g. weeks at a time). In addition, devices that are in communication with each other may communicate directly or indirectly through one or more intermediaries.

A description of an embodiment with several components or features does not imply that all or even any of such components/features are required. On the contrary, a variety of optional components are described to illustrate the wide variety of possible embodiments of the present invention(s). Unless otherwise specified explicitly, no component/feature is essential or required.

Although process steps, algorithms or the like may be described in a particular sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention(s), and does not imply that the illustrated process is preferred.

Although a process may be described as including a plurality of steps, that does not imply that all or any of the steps are preferred, essential or required. Various other embodiments within the scope of the described invention(s) include other processes that omit some or all of the described steps. Unless otherwise specified explicitly, no step is essential or required.

Although a process may be described singly or without reference to other products or methods, in an embodiment the process may interact with other products or methods. For example, such interaction may include linking one business model to another business model. Such interaction may be provided to enhance the flexibility or desirability of the process.

Although a product may be described as including a plurality of components, aspects, qualities, characteristics and/or features, that does not indicate that any or all of the plurality are preferred, essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

An enumerated list of items (which may or may not be numbered) does not imply that any or all of the items are equivalent to each other or readily substituted for each other.

All embodiments are illustrative, and do not imply that the invention or any embodiments were made or performed, as the case may be.

VI. Computing

It will be readily apparent to one of ordinary skill in the art that the various processes described herein may be implemented by, e.g., appropriately programmed general purpose computers, special purpose computers and computing devices. Typically a processor (e.g., one or more microprocessors, one or more microcontrollers, one or more digital signal processors) will receive instructions (e.g., from a memory or like device), and execute those instructions, thereby performing one or more processes defined by those instructions.

A "processor" means one or more microprocessors, central processing units (CPUs), computing devices, microcontrollers, digital signal processors, or like devices or any combination thereof.

Thus a description of a process is likewise a description of an apparatus for performing the process. The apparatus that performs the process can include, e.g., a processor and those input devices and output devices that are appropriate to perform the process.

Further, programs that implement such methods (as well as other types of data) may be stored and transmitted using a variety of media (e.g., computer readable media) in a number of manners. In some embodiments, hard-wired circuitry or custom hardware may be used in place of, or in combination with, some or all of the software instructions that can implement the processes of various embodiments. Thus, various combinations of hardware and software may be used instead of software only.

The term "computer-readable medium" refers to any medium, a plurality of the same, or a combination of different media, that participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols, such as Ethernet (or IEEE 802.3), SAP, ATP, Bluetooth™, and TCP/IP, TDMA, CDMA, and 3G; and/or (iv) encrypted to ensure privacy or prevent fraud in any of a variety of ways well known in the art.

Thus a description of a process is likewise a description of a computer-readable medium storing a program for performing the process. The computer-readable medium can store (in any appropriate format) those program elements which are appropriate to perform the method.

Just as the description of various steps in a process does not indicate that all the described steps are required, embodiments of an apparatus include a computer/computing device operable to perform some (but not necessarily all) of the described process.

Likewise, just as the description of various steps in a process does not indicate that all the described steps are required, embodiments of a computer-readable medium storing a program or data structure include a computer-readable medium storing a program that, when executed, can cause a processor to perform some (but not necessarily all) of the described process.

Where a process is described, in an embodiment the process may operate without any user intervention. In another embodiment, the process includes some human intervention (e.g., a step is performed by or with the assistance of a human).

The invention claimed is:

1. A system for evaluation of driver braking performance under emergency conditions, comprising:
   a driver measuring unit including a force measuring means and a communications means, the driver measuring unit being adapted for attachment to a road vehicle brake applicator interface and being operative to generate force measurement data representative of force applied by the driver to the brake applicator during an evaluation period and to transmit the force measurement data using the communications means;
   a vehicle measuring unit, in use carried by the vehicle, having a motion measuring means adapted to determine vehicle measurements comprising one or more of the vehicle acceleration, velocity and position, and a communications means, the vehicle measuring unit being operative to generate vehicle measurement data during the evaluation period and transmit the vehicle measurement data using the communications means; and
   a processor unit having a display screen, and communications means, wherein the processor unit is operative to receive via the communications means the force measurement data generated by the driver measuring unit and the vehicle measurement data generated by the vehicle measuring unit, and generate braking test result metrics therefrom for display on the display screen; the system characterized in that:
   the force measuring means is adapted to provide a timing trigger for the evaluation period;
   the motion measuring means comprises a combination of an inertial measurement unit for determining acceleration/deceleration measurements and a GPS receiver configured for determining one or a combination of distance/positional measurements and velocity measurements based on the Doppler-effect on a GPS carrier signal; and
   the processor unit is operative to enable selection of braking test parameters and to provide signals to the driver during a braking test procedure for the driver to act upon the provided signals and wherein the braking test result metrics comprise one or a combination of:
   driver reaction time;
   vehicle stop time;
   vehicle stop distance;
   brake pedal force;
   vehicle acceleration/deceleration; and,
   vehicle speed.

2. A system as claimed in claim 1 wherein the force measuring means of the driver measuring unit is adapted for temporary attachment to the brake applicator interface which is in the form of a brake pedal.

3. A system as claimed in claim 1 wherein the force measuring means of the driver measuring unit is adapted for temporary attachment to the brake applicator interface which is in the form of a brake handle.

4. A system as claimed in claim 1 wherein the communications means of the driver measuring unit, vehicle measuring unit and processor unit comprise short-range wireless transceivers.

5. A system as claimed in claim 1 wherein the motion measuring means of the vehicle measuring unit includes a GPS receiver capable of determining the vehicle speed, distance travelled and/or path during the evaluation period.

6. A system as claimed in claim 1 wherein the motion measuring means of the vehicle measuring unit includes an accelerometer capable of determining acceleration during the evaluation period.

7. A system as claimed in claim 1 wherein the processor unit comprises a portable computing device in the form of a smartphone or tablet computer.

8. A system as claimed in claim 1 wherein one of the processor unit and the vehicle measuring unit includes means for issuing an audible signal to signify beginning of an evaluation period.

9. A system as claimed in claim 8 wherein the processor unit includes a user interface that enables a user to select a vehicle test commencement speed.

10. A system as claimed in claim 9 wherein one of the processor unit and the vehicle measuring unit is operative to issue an audible signal following the vehicle reaching the test commencement speed as determined by the motion measuring means.

11. A system as claimed in claim 10 wherein the processor unit is operative to determine a driver reaction time based on the audible signal and force measurement data received from the driver measuring unit.

12. A system as claimed in claim 8 wherein one of the processor unit and the vehicle measuring unit is operative to issue an audible signal upon a user command.

13. A system as claimed in claim 1 further including an internet based evaluation unit adapted to receive brake test result metrics from the processor unit by way of internet communications, for comparison of collected results from different tests and evaluation against predetermined criteria.

14. A method for evaluation of driver braking performance under emergency conditions, comprising:
equipping a vehicle with a driver measuring unit a force measuring means adapted for attachment to a road vehicle brake applicator interface of the vehicle and being operative to generate force measurement data representative of force applied by the driver to the brake pedal applicator during an evaluation period wherein the driver measuring unit is adapted for transmitting the force measurement data using a communications means of the driver measuring unit;
equipping the vehicle with a vehicle measuring unit that includes a motion measuring means adapted to determine vehicle measurements comprising one or more of the vehicle acceleration, velocity and position, the vehicle measuring unit being operative to generate vehicle measurement data during the evaluation period and for transmitting the vehicle measurement data using a communications means of the vehicle measuring unit, the method characterized in that:
the force measuring means is adapted to provide a timing trigger for the evaluation period;
the motion measuring means comprises a combination of an inertial measurement unit for determining acceleration/deceleration measurements and a GPS receiver configured for determining one or a combination of distance/positional measurements and velocity measurements based on the Doppler-effect on a GPS carrier signal, and the method further comprises the steps of;
selecting braking test parameters;
initiating a braking test by providing signals to the driver in the evaluation period for the driver to act upon the provided signals;
receiving via the communications means, the force measurement data generated by the driver measuring unit and the vehicle measurement data generated by the vehicle measuring unit;
generating braking test result metrics from the received measurement data wherein the braking test result metrics comprise one or a combination of:
driver reaction time;
vehicle stop time;
vehicle stop distance;
brake pedal force;
vehicle acceleration/deceleration; and,
vehicle speed; and
displaying the generated braking test result metrics.

15. A method as claimed in claim 14 further including in response to the timing trigger for an evaluation period provided by the force measuring means, issuing a test commencement signal under control of one of the processor unit and the vehicle measuring unit, such as an audible or visual signal discernible by the vehicle driver.

16. A method as claimed in claim 15 wherein the test commencement signal is issued once the vehicle, as determined by the motion measuring means, reaches a predetermined test commencement speed.

17. A method as claimed in claim 15 wherein the generated brake test result metrics include a driver reaction time determined based on the timing of the test commencement signal and force measurement data received from the driver measuring unit.

18. A method as claimed in claim 14 including communicating the brake test result metrics to an internet based evaluation unit for comparison of collected results from different tests and evaluation against predetermined criteria.

19. A method as claimed in claim 18 wherein the internet based evaluation unit is in the form of a web site having capability to log successive testing sessions and rank against industry standards and other users, and with capability to export collated data to relevant authorities for the purpose of determining a pass or fail result for licence compliance.

* * * * *